United States Patent [19]

Margherita

[11] 4,110,076
[45] Aug. 29, 1978

[54] RADIOIMMUNOASSAY METHODS FOR THE DETERMINATION OF L-TRIIODOTHYRONINE AND THYROXINE

[75] Inventor: Salvatore S. Margherita, Manchester, Mo.

[73] Assignee: Mallinckrodt, Inc., St. Louis, Mo.

[21] Appl. No.: 713,447

[22] Filed: Aug. 11, 1976

Related U.S. Application Data

[63] Continuation of Ser. No. 590,671, Jun. 26, 1975, abandoned, which is a continuation-in-part of Ser. No. 464,345, Apr. 26, 1974, abandoned.

[51] Int. Cl.$^2$ .................. G01N 33/16; G21H 5/00
[52] U.S. Cl. .................. 23/230.6; 23/230 B; 424/1
[58] Field of Search ........... 23/230 B, 230.3, 230.6; 424/1, 12, 1.5; 250/303, 304; 252/408, 301.1 R

[56] References Cited

U.S. PATENT DOCUMENTS

| | | | |
|---|---|---|---|
| 3,673,183 | 6/1972 | Erickson | 23/253 TP X |
| 3,711,247 | 1/1973 | Adams | 25/230 B |
| 3,911,096 | 10/1975 | Chopra | 23/230 B X |
| 3,928,553 | 12/1975 | Hollander | 23/230 B X |

OTHER PUBLICATIONS

Chopra et al., J. Lab. & Clin. Med., Nov. 1972 pp. 729-739.
Mitsuma et al., Biochem. & Biophys. Res. Commun. 46, 2107 (1972).
Aloe Scientific Co. catalog 103, 1952, pp. 1010, 1028, 1029, 1088.

*Primary Examiner*—Robert M. Reese
*Attorney, Agent, or Firm*—Koenig, Senniger, Powers and Leavitt

[57] ABSTRACT

An improved, simplified radioimmunoassay method for the in vitro determination of L-triiodothyronine in unextracted blood serum involves the use of a combination reagent constituted by a buffered solution containing radioactive L-triiodothyronine and an inhibitor for inhibiting binding of L-triiodothyronine to thyroxine-binding globulin. Optionally the reagent may also include an antiserum containing antibody capable of immunoreactivity with L-triiodothyronine. Packaged test kits for use in conveniently carrying out the radioimmunoassay are also provided. Certain salts of 8-anilino-1-naphthalene sulfonic acid, which may be regarded as purified forms of the acid, are preferably employed as inhibitors for inhibiting binding of L-triiodothyronine to thyroxine-binding globulin. An improved radioimmunoassay method for the in vitro determination of thyroxine in unextracted blood serum is characterized by the use of an antiserum containing antibody capable of immunoreactivity with thyroxine and prepared from an immunogen comprising a conjugate of the N-acetyl derivative of thyroxine coupled to bovine serum albumin with 1-ethyl-3-(3-dimethylaminopropyl)-carbodiimide.

16 Claims, 2 Drawing Figures

RADIOIMMUNOASSAY METHODS FOR THE DETERMINATION OF L-TRIIODOTHYRONINE AND THYROXINE

CROSS-REFERENCE TO RELATED APPLICATION

This is a continuation of application Ser. No. 590,671, filed June 26, 1975, and now abandoned, which is a continuation-in-part of application Ser. No. 464,345, filed Apr. 26, 1974, now abandoned.

BACKGROUND OF THE INVENTION

This invention relates to radioimmunoassay methods and, more particularly to radioimmunoassay methods, reagents and packaged test kits for the in vitro determinations of L-triiodothyronine and thyroxine in unextracted blood serum.

Since the discovery in 1952 of L-triiodothyronine (3,5,3'-L-triiodothyronine or T3), this naturally occurring hormone has received attention because of its greater biological potency than thyroxine (T4) even though L-triiodothyronine is present in much smaller concentrations in blood serum than T4. It has been recognized for some time that T4 constitutes about ninety percent of the organic iodine-containing substances in the blood. After the initial demonstration of T4 in plasma, T3 was identified as the second circulating iodo-amino acid, and it has been shown that T3, like T4, is a normal thyroidal secretory product. The ease with which T3 and T4 are labeled with radioactive iodine has allowed for many studies of the detailed kinetics of metabolism of these compounds in man as well as experimental animals. Notwithstanding its low level in blood serum relative to T4, it has been estimated that T3 contributes a major portion of the calorigenic potency of the thyroid hormones. It has even been suggested that T3 is the active thyroid hormone and that T4 serves merely as precursor or pro-hormone. In any event, the determination of T3 levels must be considered in the diagnosis of thyroid disorders.

The early measurements of T3 in plasma were by extraction and purification followed by either paper chromatography, gas-liquid chromatography or displacement analysis. Because of the formidable technical difficulties encountered and the discrepancies between the various methods, the values obtained were considered only tentative. In recent years, radioimmunoassay (RIA) methods have been developed for the direct determination of T3 in unextracted blood serum. These methods are based upon the principle of competitive protein-binding (CPB) with antibody as protein binder and make possible procedures with greater inherent specificity and sensitivity than that of other in vitro thyroid tests. In accordance with the competitive inhibition principle of radioimmunoassay, unlabeled or non-radioactive antigen (T3) in unknown blood serum samples competes against radioactive labeled antigen (T3 ) for binding to antibody and thereby diminishes the binding of the labeled antigen. In order to determine the concentration of T3 antigen in an unknown sample, the degree of competitive inhibition observed in the unknown sample is compared with that obtained in known standard solutions.

As reported in the literature (Sekadde et al., Clin. Chem. 19/9, 1016-1021 (1973)), the known radioimmunoassay methods for determination of T3 depend upon the addition of a standard of unlabeled T3 or of an unknown solution to a fixed amount of T3 antibody followed by the addition of a fixed amount of radioactive labeled T3. An inhibitor to inhibit binding of T3 to thyroxine-binding globulin is also conventionally added to the mixture. The resulting mixture is typically incubated at 4° C. for 16 to 72 hours following which the antibody bound T3 is separated from the unbound T3 by any one of a number of methods. In the radioimmunoassay method for T3 described by Sekadde et al., a buffered solution containing 8-anilino-1-naphthalene sulfonic acid (ANS), an inhibitor for inhibiting binding of T3 to thyroxine-binding globulin, is added to a series of tubes by pipetting. Each of a series of standard solutions containing known amounts of T3 is added to certain of the respective tubes and unknown serum samples are added to other tubes. T3-free serum is added to all tubes containing the standard solutions. Buffer solution, antibody and radioactive T3 are then added to the tubes and the mixture incubated at 37° C. for 30 minutes. After cooling, a solution of polyethylene glycol is added to precipitate the antibody-bound T3 complex, the supernatant fluid is aspirated off and the precipitate counted with a gamma scintillation counter. The T3 value is then calculated as described. The authors state that the T3-free serum should be prepared weekly and that the buffered solution of 8-anilino-1-naphthalene sulfonic acid should be prepared daily.

Mitsuma et al. (Biochemical and Biophysical Research Communications, Vol. 46, No. 6, p. 2107-2113 (1972) describe a radioimmunoassay for the simultaneous determination of T3 and T4 in unextracted serum involving the sequential addition to glass tubes of unknown blood sample or standard T3-T4 solutions, solution of radioactive T3 and T4, inhibitor solution and antibody solution followed by incubation of the assay mixture for 90 minutes at 37° C. After incubation, separation of antibody bound T3 and unbound T3 was carried out using a solution of dextran-charcoal and the resulting two fractions counted in a gamma counter.

Other radioimmunoassay methods for the determination of T3 in unextracted blood serum involving similar procedural steps are also reported in the literature. Hufner et al., Acta Endocrinologica, 72 (1973) 464-474; Hufner et al., Clinica Chimica Acta, 44 (1973) 101-107; Hesch et al., British Medical Journal, 1973, 1, 645-648 and Docter et al., Europ. J. Clin. Invest, Abstracts, Vol. 3, No. 3, (1973) 224-225.

While certain known radioimmunoassay methods for the determination of T3 in unextracted serum may be suitable for clinical use, their usefulness is somewhat limited because such methods are time-consuming and/or require a large number of procedural operations on the part of the technician which may introduce errors and affect the accuracy or reproducibility of the assay results. Thus, the commercially available test kits for use in carrying out T3 radioimmunoassay determinations typically contain a plurality of reagents and their clinical use requires the technician to perform many time-consuming operations in preparing the reagents and/or conducting the radioimmunoassay.

As mentioned, it has been conventional in the art to utilize an inhibitor for inhibiting binding of T3 by thyroxine-binding globulin, and the use of various inhibitors such as sodium salicylate, merthiolate, dilantin and tetrachlorothyronine has been reported in the literature. The use of 8-anilino-1-naphthalene sulfonic acid as an inhibitor was proposed by Mitsuma et al., supra. However, while this compound is a potent inhibitor of the binding of T3 by thyroxine-binding globulin and has been reported as the most effective inhibitor tested to date, it suffers from the serious drawback that it also inhibits antibody binding of T3. Hüfner et al., Clinica Chimica Acta, 44 (1973) 101–107. Further, it has been found that 8-anilino-1-naphthalene sulfonic acid does not function as an effective inhibitor or yield reproducible results unless it is of the highest grade purity.

Further, known methods for the radioimmunoassay determination of T4 have involved the use of antisera against thyroglobulin (Chopra, I. J. J. Clin. Endocr. 34:938 (1972)), T4-specific antibodies against conjugates of T4 and bovine serum albumin (BSA), human serum albumin (HSA) and ovalbumin (OA) (Meinhold, H. and Wenzel, K. W., Horm. Metab. Res. 6 (1974) 169–170) and an antibody produced in response to injections of a T4-albumin conjugate (Dunn, R. T. and Foster, L. B., Clin. Chem. 19/9, 1063–1066 (1973)). However, it is desirable to have T4 antisera with greater specificity and higher avidity so as to provide greater sensitivity and improved reproducibility in the radioimmunoassay methods for the determination of T4.

SUMMARY OF THE INVENTION

Among the several objects of the invention may be noted the provision of an improved radioimmunoassay method for the determination of L-triiodothyronine in unextracted blood serum which may be conducted relatively rapidly and with fewer procedural operations being required on the part of the techncian conducting the assay; the provision of such a method which requires fewer procedural operations without affecting the sensitivity, accuracy or reproducibility of the assay results; the provision of novel combination reagents which facilitate the conduct of radioimmunoassay methods for the determination of L-triiodothyronine in unextracted blood serum; the provision of novel packaged test kits which provide practical and convenient means for the sensitive determination of L-triiodothyronine in unextracted blood serum by radioimmunoassay; the provision of an improved radioimmunoassay method for the determination of thyroxine in unextracted blood serum; the provision of such a method which provides greater specificity, sensitivity and improved reproducibility; and the provision of a novel antiserum for use in the radioimmunoassay determination of thyroxine and a novel immunogen from which such antiserum is prepared. Other objects will be in part apparent and in part pointed out hereinafter.

Briefly the invention is directed to a radioimmunoassay method for the in vitro determination of L-triiodothyronine in unextracted blood serum which comprises the steps of mixing a sample of blood serum whose L-triiodothyronine content is to be determined with a reagent consisting essentially of a buffered solution containing radioactive L-triiodothyronine and an inhibitor for inhibiting binding of L-triiodothyronine to thyroxine-binding globulin, adding to the mixture an antiserum containing antibody capable of immunoreactivity with L-triiodothyronine, incubating the resultant mixture at a temperature and for a sufficient period of time to produce substantial equilibration of the antibody bound L-triiodothyronine and unbound L-triiodothyronine, separating the unbound L-triiodothyronine from the antibody bound L-triiodothyronine, and determining the relative amounts of antibody bound radioactive L-triiodothyronine and unbound radioactive L-triiodothyronine. In another embodiment of the T3 radioimmunoassay method of the invention, the reagent with which the sample of blood serum is mixed consists essentially of a buffered solution containing radioactive L-triiodothyronine, an inhibitor for inhibiting binding of L-triiodothyronine to thyroxine-binding globulin and an antiserum containing antibody capable of immunoreactivity with L-triiodothyronine. The invention is also directed to the aforementioned reagents for use in the T3 radioimmunoassay methods of the invention.

The invention is further directed to a packaged test kit for use in such T3 radioimmunoassay methods comprising the combination of (a) a buffered solution containing radioactive L-triiodothyronine and an inhibitor for inhibiting binding of L-triiodothyronine to thyroxine-binding globulin; (b) a buffered solution containing an antiserum containing antibody capable of immunoreactivity with L-triiodothyronine; and (c) a plurality of relatively thin strips of a membrane consisting essentially of ion-exchange resin and to a packaged test kit in which buffered solution (a) additionally includes the antiserum containing antibody capable of immunoreactivity with L-triiodothyronine. Still a further feature of the invention resides in the use of the magnesium, calcium and alkali metal salts of 8-anilino-1-naphthalene sulfonic acid as purified forms of the acid as inhibitors for inhibiting binding of L-triiodothyronine to thyroxine-binding globulin.

In the T4 radioimmunoassay method of the invention, the method is carried out using an antiserum containing antibody capable of immunoreactivity with thyroxine and prepared from an immunogen comprising a conjugate of the N-acetyl derivative of thyroxine coupled to bovine serum albumin with 1-ethyl-3-(3-dimethylaminopropyl)-carbodiimide. The novel antiserum and immunogen from which it is prepared constitute additional features of this embodiment of the invention.

DESCRIPTION OF THE PREFERRED EMBODIMENTS

Figure 1:
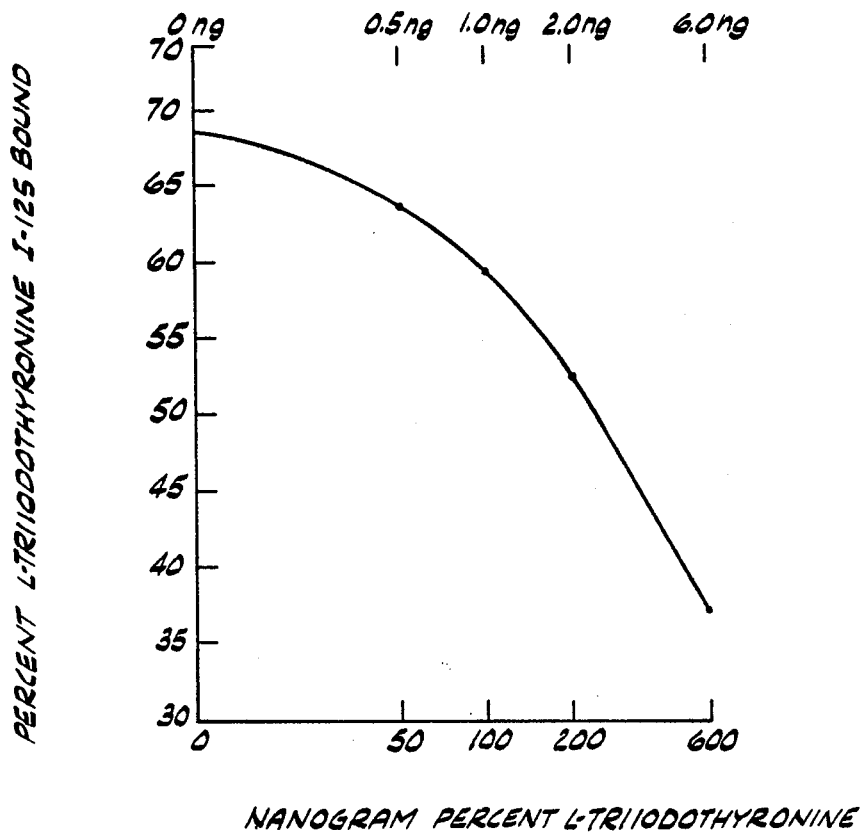
FIG. 1 is a graph depicting an illustrative standard curve obtained by plotting the percent of bound radioactive L-triiodothyronine against the concentration of standard solutions of L-triiodothyronine expressed as nanogram percent L-triiodothyronine.

In accordance with the invention, the above and other objects are accomplished through a modification of known radioimmunoassay methods for the determination of T3 in unextracted blood serum. In one embodiment of the T3 radioimmunoassay method of the invention, the first step of the radioimmunoassay method involves mixing a combination reagent with a sample of blood serum whose L-triiodothyronine content is to be determined. This combination reagent, in accordance with the invention, consists essentially of a buffered solution containing radioactive T3 and an inhibitor for inhibiting binding of T3 to thyroxine-binding globulin (TBG). It has thus been found that buffer, radioactive T3 and an inhibitor can be mixed in solution form and retain their activity even upon storage in the frozen state for reasonably long periods of time (e.g., 3 months). The use of such a combination reagent advantageously eliminates several procedural steps on the part of the technician with the attendant possibility of error being introduced thereby. It has been found that this desirable combining of reagents not only avoids time-consuming operations by the technician but accomplishes this objective without adversely affecting the accuracy, sensitivity or reproducibility of the assay.

The combination reagent contains effective and known quantities of veronal buffer solution, radioactive T3 and an inhibitor for inhibiting T3 binding to TBG. A precount determination of radioactive T3 in the reagent is made at the outset of the test on a gamma counter. The radioactive T3 with reagent is preferably T3 containing iodine-125 but T3 containing iodine-131 or other radioisotope may also be employed in the practice of the invention. The veronal buffer solution is prepared using sodium barbital and also contains a chelating agent, such as ethylenediamine tetraacetic acid for chelating unwanted metal ions and a preservative such as sodium azide. Preferably, the buffer solution has a pH of 8.6–8.8.

As the inhibitor component of the reagent, any of the various inhibitors known to the art may be used. Among these may be mentioned sodium salicylate, merthiolate, dilantin, tetrachlorothyronine and 8-anilino-1-naphthalene sulfonic acid. However, the latter inhibitor has been reported as inhibiting antibody binding of T3. Also, unless of high purity, 8-anilino-1-naphthalene sulfonic acid yields irreproducible results. In accordance with the invention, it has now been found that the magnesium, calcium and alkali metal salts of 8-anilino-1-naphthalene sulfonic acid are effective inhibitors for inhibiting T3 binding to TBG and do not significantly inhibit antibody binding of T3, these salts thus being regarded as purified forms of 8-anilino-1-naphthalene sulfonic acid. The magnesium salt is the preferred inhibitor for use in the radioimmunoassay methods and reagents of the present invention although the other salts may likewise be used. In preparing magnesium 8-anilino-1-naphthalene sulfonate as described hereinafter, the free acid starting material should be free of tarry products. The calcium and alkali metal salts (e.g., sodium and potassium) may be prepared by similar methods. When stored in a desiccator at −20° C., the magnesium salt of 8-anilino-1-naphthalene sulfonic acid is stable for at least 4 months.

After the unknown sample of blood serum has been mixed with the combination reagent, an antiserum containing antibody capable of immunoreactivity with T3 is added to the resultant mixture. The antibody present has a specificity for T3 but is not capable of in vitro immunoreactivity with T4 or mono- and diiodotyrosine. Thus, the quantity of radioactive T3 bound by a given quantity of antibody is decreased in the presence of unlabeled T3 from the unknown blood serum sample, and the effect is directly related to the concentration of the unlabeled hormone.

Methods known to the art may be employed for producing antisera containing antibody capable of immunoreactivity with T3 for use in the present invention. For example, an antiserum containing very specific antibodies against T3 may be prepared by the method described by Hesch & Hüfner, European Thyroid Association, Bern (1971) and Acta biol. med. germanica 28 (1972) 351 and by Hüfner and Hesch, Acta endocr. 72 (1973) 464–474. This antiserum is produced by the injection into rabbits of T3-methyl ester hydrochloride conjugated to bovine serum albumin (BSA) via the 1-ethyl-3-(3-dimethylaminopropyl) carbodiimide procedure known to the art. The preparation of an antiserum having an antibody with excellent specificity for T3 is produced by injection into rabbits of T3 coupled to bovine serum albumin with carbodiimide. Siegel et al., J. Clin. Endoc. 37: 526–32, 1973. Useful antiserum containing antibody capable of immunoreactivity with T3 may also be produced through the use of the N-acetyl derivative of T3 coupled to bovine serum albumin with carbodiimide. The use of this conjugate or the T3-methyl ester hydrochloride-BSA conjugate as the immunogen for the production of useful antisera is preferred since these conjugates prevent the formation of T3-T3 complexes by eliminating the free amino group or free carboxyl group of T3. It will be understood that other antisera containing antibodies with a specificity for T3, such as those produced through the use of T3-human serum albumin conjugates, may also be used in the practice of the invention. For use in the radioimmunoassay methods of the invention, it is preferred that the antiserum be diluted to the extent that 60–75% of a tracer quantity of radioactive T3 is bound, i.e., a dilution of greater than 1:100.

Once the antiserum has been added to the mixture of the blood serum sample and the combination reagent described above, the resultant mixture is incubated at a temperature and for a sufficient period of time to produce substantial equilibration of the antibody bound T3 and unbound T3. During incubation, the antibody in the diluted antiserum forms an immune complex in the presence of the radioactive T3 and serum T3 (or T3 standard solutions). Conventionally, in radioimmunoassay methods for the determination of T3, the mixture is incubated at 4° C. for 16 to 72 hours although shorter incubation periods at 37° C. have been reported (Sekadde et al., supra). While conventional incubation times and temperatures may be employed in carrying out the present invention, it is preferred that the incubation step be conducted at a temperature of 37° C. for a period of approximately one hour after which binding of T3 by the antibody has been found to reach substantial equilibrium.

Upon completion of the incubation step, the unbound T3 is separated from the antibody bound T3. Separation may be effected in various ways known to the art. Thus, unbound T3 and antibody bound T3 may be separated, for example, by incubating the mixture with a second antibody to precipitate the antibody bound fraction. The antibody bound fraction may also be nonspecifically precipitated by materials such as ammonium sulfate, sodium sulfate and trichloroacetic acid and by solvents such as dioxane, ethyl alcohol, acetone or polyethylene glycol. Further, separation of the bound and free radioactive T3 may be accomplished by adsorption by substances such as dextran-coated charcoal, talc, kaolin and anion-exchange resins in granular form.

In the preferred embodiment of the invention, separation is conveniently effected through contacting of the mixture with a relatively thin strip of a membrane consisting essentially of an ion-exchange resin for a period of approximately one hour at room temperature. The ion-exchange resin membranes which may be employed in the present invention are relatively thin strips, sheets or films of a solid hydrous gel consisting of an insoluble polymeric matrix to which are attached dissociable cationic or anionic groups, the gel being preferably reinforced with some suitable fibrous material. Many useful resin membranes of this kind are known, as for example those described in U.S. Pat. Nos. 2,730,768, 2,780,604, 2,800,445 and 2,860,097. For example, a commercially available anion-selective resin useful in the present invention is that marketed under the trade designation "AR-111" (by Ionics, Inc. of Watertown, Mass.).

Upon addition of the resin strips to the test and standard or control vials, the vials are capped and the contents incubated as by rotating the vials for one hour at room temperature. The rotation time should be the same for the unknown and control samples. At the end of the incubation period, the resin strips are removed as by means of forceps and discarded.

The relative amounts of antibody bound radioactive T3 and unbound radioactive T3 are then determined. Preferably, this is accomplished by a determination of the radioactive T3 in each vial by means of a gamma counter. The count rate of vial components following removal of the resin strip reflects the serum concentration of T3. The percent of radioactive T3 which is antibody bound is then calculated as follows:

$$\frac{\text{Net CPM Postcount}}{\text{Net CPM Precount}} \times 100 = \% \text{ T3 I-125 Bound to Antibody}$$

With increasing quantities of nonradioactive T3 (patient or standard), the percent radioactive T3 bound by the antibody decreases. Based upon this principle, a standard curve (see FIG. 1 for illustrative standard curve) is prepared by plotting the percent radioactive T3 bound by each of a series of T3 standards versus its respective T3 concentration. The patient's total circulating serum T3 concentration is then readily determined by comparing the percent radioactive T3 bound in the patient's serum sample to the standard curve.

In a second embodiment of the T3 radioimmunoassay method of the invention, the combination reagent with which the unknown blood serum sample is mixed as the first step of the radioiumunoassay determination of T3 is constituted by a buffered solution containing radioactive T3, an inhibitor for inhibiting binding of T3 to thyroxine-binding globulin and an antiserum containing antibody capable of immunoreactivity with T3. The remaining steps of the method are as described above in connection with the first embodiment of the invention. The radioimmunoassay method of the second embodiment is particularly advantageous for use by hospitals, clinical laboratories and the like which conduct a large number of radioimmunoassay T3 determinations daily or weekly. The novel combination reagent containing buffer, radioactive T3, inhibitor and T3 antiserum in accurate and effective amounts can be prepared in bulk in sufficient volume to satisfy the requirements of the institution or laboratory for a given period such as a day or a week. The radioimmunoassay method is then initiated by simply mixing a sample of blood serum whose T3 content is to be determined with the reagent and proceeding with the other steps of the method as previously described. The use of the combination reagent thus eliminates procedural steps on the part of the technician in the preparation and combining of individual reagents (e.g., as by pipetting) and thereby eliminates important sources of technician error.

In the past, the art has operated on the accepted premise that the reaction between T3 and T3 antibody is irreversible and therefore the antiserum was not added or combined with the other components of the test system until the T3 radioimmunoassay was actually being conducted. However, in accordance with the present invention it has unexpectedly been found that when the antiserum is combined with the buffered solution containing the radioactive T3 and inhibitor, the immunoreaction between T3 and antibody contained in the antiserum still proceeds when the mixture of the unknown blood sample and combination reagent is incubated, as for example and preferably, at 37° C. for approximately one hour. In particular, it has been found that such a combination reagent may be effectively employed in the radioimmunoassay method of the invention under these preferred incubation conditions for a period of up to about 10 days after preparation of the reagent. Beyond this period, it becomes necessary to incubate the mixture of the unknown blood serum sample and combination reagent for longer time periods (e.g., 3 hours or more).

For use in carrying out the T3 radioimmunoassay method of the invention, packaged test kits containing the necessary reagents and materials are provided. For the practice of the first embodiment described above, the essential components of the preferred packaged test kit include a buffered solution containing radioactive T3 and an inhibitor, a buffered solution containing an antiserum and a plurality of relatively thin strips of an ion-exchange resin membrane. For the practice of the second embodiment described above, the preferred packaged test kit includes the combination reagent containing buffer, radioactive T3, an inhibitor and an antiserum together with a plurality of ion-exchange resin membrane strips. Both kits may also include a plurality of solutions of T3-depleted serum containing varying amounts of T3 and a barbital buffer solution adapted to provide a pH of 8.6–8.8.

In accordance with the T4 radioimmunoassay method of the invention, it has now been found that improved results are obtained through the use of an antiserum prepared from an immunogen comprised of a conjugate of the N-acetyl derivative of thyroxine coupled to bovine serum albumin with 1-ethyl-3-(3-dimethylaminopropyl)-carbodiimide. With this antiserum, greater specificity than that of other T4 antibodies is realized and, in addition, greater avidity, i.e., tightness of binding between the antigen and antibody in the antiserum. This, in turn, provides greater sensitivity and reproducibility in test results.

The novel antiserum and novel immunogen produced as described hereinafter, through the present invention, make possible the realization of improved sensitivity and reproducibility in the test method results. For example, in a comparison study between an antiserum of this invention and one prepared with free thyroxine rather than the N-acetyl derivative of thyroxine, the results showed that the former gave a standard deviation roughly one-fifth that of the latter. With the use of this novel antiserum, the variation in recovery values of T4 is thus lower.

In carrying out the T4 radioimmunoassay method of the invention, a sample of blood serum whose thyroxine content is to be determined is first mixed with a reagent consisting essentially of a buffered solution containing radioactive thyroxine and an inhibitor for inhibiting binding of thyroxine to thyroxine-binding globulin. As the inhibitor, any of the inhibitors previously mentioned in connection with the T3 test method may be used.

Next, there is added to the mixture the aforementioned novel antiserum which is prepared, as described hereinafter, from a novel immunogen comprising a conjugate of the N-acetyl derivative of thyroxine coupled to bovine serum albumin with 1-ethyl-3-(3-dimethylaminopropyl)-carbodiimide. The resultant mixture is incubated at a temperature and for a sufficient period of time to produce substantial equilibration of the antibody bound T4 and unbound T4. Preferably, in the present T4 radioimmunoassay invention, the incubation step is conducted at a temperature of 37° C. for a period of approximately thirty minutes. Longer incubation periods may be employed but are not advantageous.

After the incubation step has been completed, the unbound T4 is separated from the antibody bound T4. Separation may be effected through any of the various means previously described in connection with the T3 radioimmunoassay test method, but preferably is effected through contacting of the mixture with a relatively thin strip of a membrane consisting essentially of an ion-exchange resin for a period of approximately thirty minutes at room temperature. The ion-exchange resin membranes disclosed above are useful for this purpose. At the end of the incubation period, the resin strips are removed from the test and standard vials as by means of forceps and discarded.

The relative amounts of antibody bound radioactive T4 and unbound radioactive T4 are then determined. This may be accomplished by a determination of the radioactive T4 in each vial by means of a gamma counter. The count rate of vial components following removal of the resin strip reflects the serum concentration of T4. The percent of radioactive T4 which is antibody bound is then calculated as follows:

$$\text{Percent Thyroxine I-125 Bound} = \frac{\text{Net CPM Postcount}}{\text{Net CPM Precount}}$$

Figure 2:
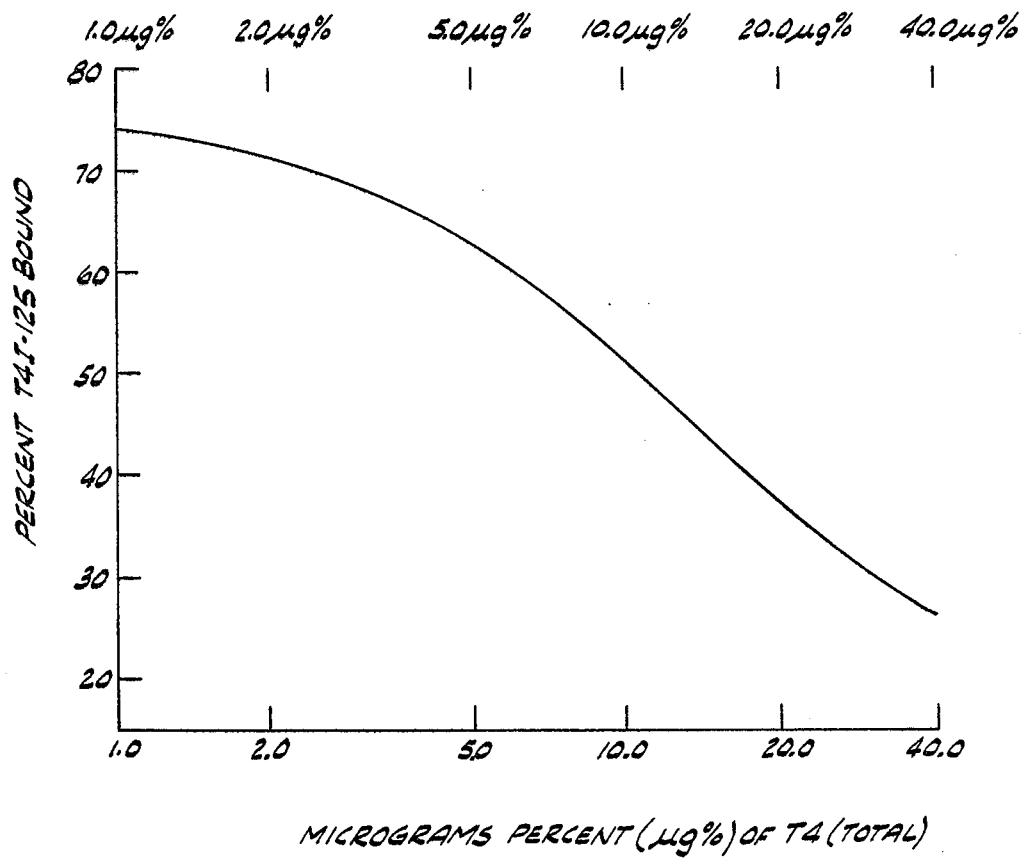
FIG. 2 is a graph depicting an illustrative standard curve obtained by plotting the percent of bound radioactive thyroxine against the concentration of standard solutions of thyroxine expressed as micrograms percent thyroxine.

With increasing quantities of nonradioactive T4 (patient or standard), the percent radioactive T4 bound by the antibody decreases. In accordance with this principle, a standard curve (FIG. 2 is an illustrative standard curve) is prepared by plotting the percent radioactive T4 bound by each of a series of T4 standards versus its respective T4 concentration. The patient's total serum thyroxine is then readily determined by comparing the percent radioactive T4 bound in the patient's serum sample to the standard curve.

Packaged test kits are provided for carrying out the T4 radioimmunoassay test method of the invention. The kits include a buffered solution containing radioactive thyroxine and an inhibitor for inhibiting binding of thyroxine to thyroxine-binding globulin, a buffered solution containing the novel T4 antiserum and a plurality of relatively thin strips of an ion-exchange resin membrane.

The invention is further illustrated by the following:

EXAMPLE 1

The following illustrates the practice of the T3 radioimmunoassay test method of the invention.

Sodium Barbital (Veronal) Buffer

A 0.05M veronal buffer solution having a pH of 8.6–8.8 was prepared by adding sodium barbital (10.3 g.) to distilled water (900 ml.) in a liter beaker and the sodium barbital dissolved by mechanical stirring with gentle warming. Hydrochloric acid (2N) was added dropwise until the pH reached 8.70±0.05. The solution was transferred to a 1 liter volumetric flask and sodium azide (100 mg.) added as a preservative. Ethylenediaminetetraacetic acid (0.3722 g.) was added and dissolved with stirring. The solution was diluted to a final volume of 1 liter and stored at 4° C. to 10° C. For use as antibody diluent containing 0.1% (w/v) human serum albumin (HSA), heat inactivated HSA solution (4 ml. 25% w/v; 52° C.±2° C. for 30 minutes) was added before adjusting to final volume.

Preparation of Magnesium 8-Anilino-1-Naphthalene Sulfonate

8-Anilino-1-naphthalene sulfonic acid (30 g.) of a high grade of purity (Eastman Kodak Co.) was added to distilled water (600 ml.) contained in an 800 ml. beaker provided with a stir bar. Sodium hydroxide (5N) was added dropwise while the mixture was being heated with stirring. Solubilization occurs from approximately 75° C. to 85° C. with the addition of approximately 16 ml. of sodium hydroxide. The hot solution was gravity filtered through coarse sintered glass and the filtrate was collected in a wide mouth beaker and cooled to 10° C. To the filtrate was added with stirring a saturated aqueous solution of magnesium chloride (20 ml.) causing precipitation of magnesium 8-anilino-1-naphthalene sulfonate. After standing for 10–15 minutes at 8°–10° C., the precipitate was suction filtered through coarse sintered glass, followed by washing with ice cold water (300 ml.). The precipitate was redissolved in water (300 ml.) with stirring and heat (75° C.). Upon solution, the solution was immersed in an ice bath and allowed to stand for 30–45 minutes. The crystals were suction filtered through coarse sintered glass, followed by washing with ice cold water (300 ml.). The crystals were again redissolved in water (300 ml.) with stirring and heat (75° C.) and crystallization effected by rapid cooling as before. The material was again suction filtered through coarse sintered glass followed by washing with ice cold water (300ml.). The magnesium 8-anilino-1-naphthalene sulfonate was dried in a desiccator in the dark to constant weight and stored in an amber container. The yield was 27.5 g. or 91.6%.

The efficacy and optimal quantity of magnesium 8-anilino-1-naphthalene sulfonate to be used in the T3 radioimmunoassay test method are determined as follows: 1. A solution of magnesium 8-anilino-1-naphthalene sulfonate (containing 3 mg./ml. (w/v)) in 0.05M veronal buffer (pH 8.6 to 8.8) was prepared. Vigorous stirring is required to dissolve the magnesium 8-anilino-1-naphthalene sulfonate. To a series of 5 vials, 0.05, 0.10, 0.15, 0.20 and 0.30 ml., respectively, of the magnesium 8-anilino-1-naphthalene sulfonate solution was added. To a sixth vial, 0.3 ml. of the veronal buffer solution was added. To each vial, normal human serum (100 µl.) was added. To each vial was also added radioactive L-triiodothyronine containing iodine-125 ($^{125}$I-T3; 40–60 pg. of specific activity 350–600 mCi/mg.) in veronal buffer. A precount was determined for each vial using a gamma scintillation well counter.

2. All vials were incubated at 37° C. for 1 hour (static).

3. To all vials, veronal buffer solution (1.0 ml.) was added.

4. A strip of ion-exchange resin (anion-selective resin marketed under the designation "AR-111" by Ionics, Inc.) was added to each vial and the vial caps replaced.

5. The vials were rotated for 1 hour at room temperature (15° C. to 32° C.).
6. The strips were carefully removed from the vials and discarded.
7. The count rate was determined for each vial.
8. On linear graph paper the % $^{125}$I-T3 bound $$(\frac{\text{post CPM}}{\text{pre CPM}} \times 100)$$

vs. the quantity of magnesium 8-anilino-1-naphthalene sulfonate (μg.) added is plotted. The resultant curve should show a maximum effect (minimum % radioactive T3 bound) at 240–300μg. ANS inhibitor.
9. The percentage inhibition is calculated as follows:

$$\frac{\% \text{ T3* bound without ANS} - \% \text{ T3* bound at ANS max}}{\% \text{ T3* bound without ANS}} \times 100$$

The allowable limits of inhibition are 50% or greater.

Preparation of High Specific Activity $^{125}$I-T3

To a reaction vial containing Na I$^{125}$ (12 mCi) were added 1 drop of 1:9::H$_2$SO$_4$:H$_2$O and 1 drop of saturated Na$_2$HPO$_4$. Nonradioactive T3 as the free acid (20μl. of predetermined purity) was dissolved in a mixture of 1:1 NH$_4$OH: methanol at a concentration of 0.5 mg./ml. After mixing, the pH was checked using pHydrion paper. The pH must be 7.5–8.5. If pH adjustment is necessary, NaOH or H$_2$SO$_4$ (1:9) is used. With mixing, saturated I$_2$ (4μl.) was added to the reaction vial. The reaction was allowed to continue for 25 seconds. 6 drops of a sodium sulfite solution (containing 100 mg./ml.) were added. The mixture (10μl.) was chromatographed on paper using a solvent system of 150 mg. sodium sulfite: 227 ml. formic acid: 773 ml. H$_2$O. The $^{125}$I-T3 was separated from other reaction components by thin layer chromatography.

Allowable limits of strength — 350–600mCi/mg.

The haptenic specificity of $^{125}$I-T3 prepared as above was tested as follows: Standardized T3 antiserum was diluted in veronal buffer 1:5 and 1:10. To three vials (run in duplicate) were added 0.1 ml. undiluted antiserum and 0.1 ml. of each dilution in buffer. The $^{125}$I-T3 was diluted to 400–600 pg./ml. in veronal buffer and 0.1 ml. added to each vial. The volume was brought to 1.2 ml. with veronal buffer. A precount was determined for each vial. The vials were incubated statically at 37° C. for 1 hour. Veronal buffer (1 ml.) was added to each vial as was a strip of ion-exchange resin. The vials were rotated at room temperature (15° C. to 32° C.) for 1 hour and the strips carefully removed. The vial contents were counted and the % $^{125}$I-T3 bound was determined:

$$\frac{\text{CPM post}}{\text{CPM pre}} \times 100$$

The specificity is suitable for the T3 radioimmunoassay method of the invention when both dilutions show greater than 50% binding, but it is preferred that the binding of undiluted T3 antiserum is 85–100%.

Preparation of T3-Depleted Serum

T3 is extracted from normal human serum according to the following procedure:

1. Fines are removed from ion-exchange resin (80 g. "Amberlite CG-400" marketed by Rohm and Haas Company) by suspension in water.
2. The resin is then equilibrated using 0.05M barbital buffer, pH 8.6.
3. A slurry of resin is prepared in buffer and poured into a chromatographic column, forming a bed 27 cm wide by 35 cm high.
4. A sufficient quantity of high specific activity $^{125}$I-T3 is added to the serum to yield 40,000–60,000 cpm/ml.
5. Sodium azide is dissolved in the serum to a concentration of 0.1%.
6. The serum is passed through the column and fractions are collected.
7. Aliquots of fractions are counted for extraction efficiency which must be greater than 97.5%.

The T3 depleted serum prepared as above is then tested for binding capacity in order to evaluate thyroxine-binding globulin (TBG) content after extraction as follows:

Veronal buffer (1.0 ml.) is added to each of 3 vials (run in duplicate). 100μl. $^{125}$I-T3 (50 pg.) is added to each vial. To one vial, T-3 depleted serum (100μl.) is added. To a second vial, an euthyroid control serum (100μl.) is added and to the third vial is added a hyperthyroid control serum (100μl.). The vials are mixed by rotation for 1 minute and all vials are precounted. The vials are incubated at 37° C. for 1 hour (H$_2$O bath, static). Veronal buffer (1 ml.) is added. A strip of ion-exchange resin is inserted into each vial and the vials are rotated for 1 hour at room temperature. The strips are carefully removed and the vial contents are counted.

The % T3* bound for each vial is calculated as follows:

$$\frac{\text{CPM Post}}{\text{CPM Pre}} \times 100 = \% \ ^{125}\text{I-T3 bound}$$

An increasing count rate should be observed in the order.

Hyperthyroid < Euthyroid < T3-depleted The Δ percent increase from the euthyroid control to T3-depleted should be 8% or greater.

The T-3 depleted serum is stored at 4° C. until the T3 standards are prepared, preferably the same day.

Preparation of T3 Standards

T3 in free acid form is the starting material. A solution of the T3 in methanolic NH$_4$OH is chromatographed to determine the absence of T4. The standard solutions are prepared as follows:

1. 10 mg. of T3 which has been stored in a desiccator (at −20° C. to −30° C.) is accurately weighed out and transferred to a 100 ml. volumetric flask.
2. A mixture of methanol and concentrated NH$_4$OH (99:1) is prepared and approximately 100 ml. is added to the volumetric flask.
3. The mixture is stirred until the T3 is completely dissolved and 8.c. ad. 100 ml. with the methanol-ammonium hydroxide solution. The concentration is 100μg./ml.
4. 1 volume of 100μg./ml. T3 is diluted with 99 volumes of veronal buffer (0.05 M: pH 8.6–8.8). The concentration is 1μg. T3/ml.

The following quantities of 1μg./ml. solution are used to prepare 25 ml. of T3 standards containing 0, 0.5, 1.0, 2.0 and 6.0 ng./ml. T3. To four 25 ml. volumetric flasks add approximately 15 ml. T3-depleted serum as prepared above. To these flasks were added the following volumes of T3 solution containing 1,000 ng./ml.: 12.5μl., 25μl., 50μl. and 150μl., respectively. q. s. ad. 25 ml. with T3-depleted serum.

Preparation of T3 Antiserum and evaluation for titer

T3 antiserum was prepared by hyperimmunization of rabbits or goats with T3-methyl ester hydrochloride + BSA immunogen emulsified in complete Freund's adjuvant as described in the literature previously mentioned. The antisera is evaluated for titer as follows:

Antisera are stored in lyophilized form. The T3 antiserum (0.2 cc.) is reconstituted by adding veronal buffer (5 ml.) containing 0.1% HSA prepared as described above. The 5 ml. constitutes a 1:25 dilution of antiserum. Add 1.25 ml. of the 1:25 dilution to 3.75 ml. of 0.1% HSA buffer to provide a 1:100 dilution. To 6 vials (run in duplicate), add 0.8 ml. veronal buffer and then add consecutively in the order given (a) 100μl. of magnesium 8-anilino-1-naphthalene sulfonate solution, (b) 100μl. T3-depleted serum and (c) 100μl. of $^{125}$I-T3 solution (400-600 pg./ml.).

Serial 5-fold dilutions of T3 antiserum beginning with the 1:100 dilution are prepared as follows:

To 5 test tubes (5 ml. capacity) add 0.8 ml. veronal buffer (containing 0.1% HSA) and number the tubes. Add 0.2 ml. of the 1:100 dilution to the first tube (dilution 1:500); transfer 0.2 ml. of the 1:500 dilution to the second tube and mix (dilution 1:2500). Continue the serial 5x dilutions to give 1:12,500, 1:62,500 and 1:312,500. The tubes now contain 0.8 ml. of varying antiserum dilutions as follows (except the last tube which contains 1.0 ml.):

| Tube # | 1 | 2 | 3 | 4 | 5 |
|---|---|---|---|---|---|
| Dilution Antiserum | 500 | 2,500 | 12,500 | 62,500 | 312,500 |

Add 100μl. of the 1:100 dilution to the first rx vial and 100μl. of each dilution above to the remaining 5 rx vials. Mix the vial contents for 1 minute and precount with a gamma counter. Incubate all vials at 37° C. (H₂O bath) for 1 hour. Add veronal buffer (1.0 ml. without HSA) to each vial; add an ion-exchange resin strip to each vial and rotate the vials for 1 hour at room temperature (15° C. to 32° C.). The resin strips are carefully removed and the vial contents counted for $^{125}$I-T3. The %T3* bound for each dilution is calculated as follows:

$$\frac{\text{Post count}}{\text{Pre count}} \times 100 = \% \, ^{125}\text{I-T3 bound}$$

A graph is prepared on linear graph paper relating dilution of antiserum vs. % T3* bound. For use in the assay, the dilution giving 75% binding is selected. The 50% binding end-point is useful in comparing various antisera.

Preparation of Kit Components and Kit

A. Reaction vials: To 8 parts veronal buffer add 1 part of magnesium 8-anilino-1-naphthalene sulfonate (3 mg./ml.) and 1 part $^{125}$I-T3 solution (400-600 pg./ml.). Mix mechanically for 1 minute and transfer to an automatic pipetter or dispensing device. 1 ml. of the above prepared combination reagent is transferred to each reaction vial and the vials are stored at −20° C. (or lower).

B. T3 depleted serum-T3 standards prepared as described above.

C. T3 antiserum diluted as described above to contain the dilution antibody binding 75% of a 40-60 pg. quantity of $^{125}$I-T3.

D. Veronal buffer prepared as described.

E. Ion-exchange resin strips.

A typical packaged test kit contains the following components:

1. 100 reaction vials containing 1 ml. each of the combination reagent.
2. Vials containing T3 standards diluted in T3 depleted serum — 1.5 ml. each of the 0, 0.5, 1.0, 2.0 and 6.0 ng./ml. T3 standards.
3. T3 antiserum — 5 vials containing 2.5 ml. each, prediluted.
4. Veronal buffer — 1 container with 110 ml. veronal buffer (0.05 M, pH 8.6-8.8).
5. 2 containers, each with 50 ion-exchange resin strips in saline solution.

Components 1, 2 and 3 are stored and shipped in the frozen state. Components 4 can be stored at 3°-5° C. or frozen. Component 5 is not allowed to be frozen and may be stored at room temperature.

T3 Radioimmunoassay Test Method

The following procedure is employed in carrying out the T3 radioimmunoassay method of the invention.

1. The required number of reaction vials is removed from the freezer and the net precount per minute is determined for each vial during or after thawing. The thawed reaction vials are gently agitated. Preferably, the test is carried out in duplicate.
2. 100 microliters each of the 0. 0.5, 1.0, 2.0 and 6.0 ng./ml. T3 standards is added to reaction vials and 100 microliters of patient's blood serum is added to each of the other reaction vials.
3. 100 microliters of T3 antiserum is added to each of the reaction vials and the caps replaced.
4. The vial contents are mixed by rotating for one minute on a rotator at 12-14 rpm or by gently agitating the vial rack.
5. The reaction vials are incubated in a water bath at 37° C. for one hour ± 5 minutes. The vials should be incubated in a water bath at such depth that the level of liquid in the reaction vial is equalled or exceeded.
6. Veronal buffer (1.0 ml.) is added to each vial.
7. One ion-exchange resin strip is inserted in each reaction vial and the caps replaced.
8. The reaction vials are rotated for one hour at ambient temperature (15° C. to 32° C.) on a rotator which produces end-over-end mixing at 12-14 rpm.
9. The resin strips are carefully removed and discarded. The resin strips should be allowed to drain over the vials by touching the strip lightly on top of the vial prior to replacing the vial caps.
10. The net postcount per minute is determined for each reaction vial.
11. The % T3 I-125 bound is calculated by dividing the net CPM postcount by the net CPM precount and multiplying by 100

$$\frac{\text{Net CPM Postcount}}{\text{Net CPM Precount}} \times 100 = \%\text{T3 I-125 bound to antibody}$$

12. The % T3 I-125 bound is plotted on the linear axis (ordinate) of semilog graph paper vs. concentration of standards as ng. % T3.

13. From the standard curve thus obtained, one can read the concentration of total circulating T3 in the patient's blood serum from its % T3 I-125 bound.

The standard curve shown in FIG. 1 was prepared by plotting the following numbers:

| T3 Standard ng. % | Net CPM Precount | Net CPM Postcount | % T3 I-125 Bound (% B) |
|---|---|---|---|
| 0 | 16936 | 11568 | 68.3 |
| 50 | 16835 | 10738 | 63.8 |
| 100 | 16670 | 9918 | 59.5 |
| 200 | 16921 | 8906 | 52.6 |
| 600 | 16799 | 6316 | 37.6 |

Employing the above-described radioimmunoassay method, the euthyroid range was found to be 72–214 ng.% T3* with a mean of 126±29, the mean for hyperthyroid patients was found to be 480±127 ng.% and the mean for hypothyroid patients was found to be 67±46 ng.%. Utilizing this normal range, serum T3 was found to be elevated in 98% of the patients who were clinically hyperthyroid and serum T3 was found to be below the normal range in 56 percent of the patients who were clinically hypothyroid.

The following data were obtained using the radioimmunoassay method described above and represent the mean and standard deviation for each set of 6 replicate determinations made on each of 4 different days for a euthyroid control serum and a hyperthyroid control serum.

Intra-assay variation

Euthyroid Control Serum n=6

|  | Run 1 | Run 2 | Run 3 | Run 4 |
|---|---|---|---|---|
| Mean T3 value (ng. %) | 119.0 | 124.0 | 121.6 | 117.4 |
| Standard deviation (ng. %) | 7.6 | 10.7 | 10.1 | 6.5 |

Hyperthyroid Control Serum n = 6

|  | Run 1 | Run 2 | Run 3 | Run 4 |
|---|---|---|---|---|
| Mean T3 value (ng. %) | 245.8 | 267.3 | 267.5 | 255.8 |
| Standard deviation (ng.%) | 6.3 | 11.2 | 16.8 | 19.3 |

Inter-assay variation

|  | Euthyroid Control Serum (ng. % T3*) | Hyperthyroid Control Serum (ng. % T3*) |
|---|---|---|
| Day 1 | 119.0 | 245.8 |
| Day 2 | 124.0 | 267.3 |
| Day 3 | 121.6 | 267.5 |
| Day 4 | 117.4 | 255.8 |
| Mean | 120.6 | 259.1 |
| Standard deviation | 2.8 | 10.4 |

*Each value represents the mean of six determinations.

EXAMPLE 2

The following illustrates the practice of the T4 radioimmunoassay test method of the invention:

Sodium Barbital (Veronal) Buffer

A 0.075M veronal buffer solution having a pH of 8.6–8.8 was prepared by adding sodium barbital (dehydrated form) to distilled water (900 ml.) in a liter beaker, the amount of sodium barbital providing 15.45 g./l. The sodium barbital was dissolved with stirring. Sodium azide (100 mg.) was added as a preservative and ethylenediaminetetraacetic acid (1.86 g.) was added and dissolved with stirring. The pH was adjusted to 8.6–8.8 by the addition of acid or base and the solution diluted to a final volume of 1 liter and stored at 4° C. For use as antibody diluent containing 0.1% (w/v) human serum albumin (HSA), heat inactivated HSA solution (4 ml. 25% w/v; 52° C. ± 2° C. for 60 minutes) was added before adjusting to final volume.

Preparation of Magnesium 8-Anilino-1-Naphthalene Sulfonate

8-Anilino-1-naphthalene sulfonic acid (10 g.) of a high grade of purity (Eastman Kodak Co.) was added to distilled water (200 ml.) contained in a 500 ml. beaker. Sodium hydroxide (5N) was added from a burette dropwise while the mixture was being stirred mechanically over a hot plate. Solubilization occurs at from 75° C. to 85° C. with the addition of approximately 5.5 ml. of the sodium hydroxide solution. The hot solution was gravity filtered through coarse sintered glass and the filtrate was collected in a beaker and cooled to 10° C.–20° C. To the filtrate was added with stirring a quantity of a saturated aqueous solution of magnesium chloride such that maximum precipitation occurred (generally 6–7 ml.). The precipitate was filtered through coarse sintered glass with suction and the residue washed with ice cold water. The crude magnesium 8-anilino-1-naphthalene sulfonate was dissolved in distilled water (150 ml.) with heat (75°–85° C.) and crystallization was effected by rapid cooling. The time required for substantially complete crystallization to occur was about 30–45 minutes. The material was then filtered with suction and the residue was washed with ice cold water. A second crystallization was required. The green to yellow magnesium 8-anilino-1-naphthalene sulfonate was dried in air on a watch glass to constant weight and stored at −20° C. to −30° C. in a desiccator (amber container).

The efficacy and optimal quantity of magnesium 8-anilino-1-naphthalene sulfonate to be used in the T4 radioimmunoassay test method are determined as follows:

1. A solution of magnesium 8-anilino-1-naphthalene sulfonate (containing 6 mg./ml.) in 0.075M veronal buffer (pH 8.6-8.8). Vigorous stirring is required to dissolve the magnesium 8-anilino-1-naphthalene sulfonate. To a series of 5 vials, 0.05, 0.10, 0.15, 0.20 and 0.30 ml., respectively, of the magnesium 8-anilinp-1-naphthalene sulfonate solution was added. To a sixth vial, 0.3 ml. of the veronal buffer solution was added. To each vial, normal human serum (10μl.), which had been extracted with an ion-exchange resin, was added. To each vial was also added radioactive thyroxine containing iodine-125 ($^{125}$I-T4; 100 pg. ± 20 pg. from a 350–700 mCi/mg. preparation) in veronal buffer. The volume of each vial was brought to 1.2 with veronal buffer. A precount was determined for each vial using a gamma scintillation well counter.

2. All vials were incubated at 37° C. for one-half hour (static).

3. A strip of ion-exchange resin (quaternary ammonium type marketed by Ionics, Inc.) was added to each vial and the vial caps replaced.
4. The vials were rotated for one-half hour at room temperature (15° C. to 32° C.).
5. The strips were carefully removed from the vials and discarded.
6. The count rate was determined for each vial.
7. On linear graph paper the % $^{125}$I-T4 bound $$\left(\frac{\text{post CPM}}{\text{pre CPM}} \times 100\right)$$

vs. the quantity of magnesium 8-anilino-1-naphthalene sulfonate (μg.) added is plotted. The resultant curve should show a maximum effect (minimum % radioactive T4 bound) at 500–600 μg. ANS inhibitor.
8. The percentage inhibition is calculated as follows:

$$\frac{\% \text{ T4* bound without ANS} - \% \text{ T4* bound at ANS max}}{\% \text{ T4* bound without ANS}} \times 100 = \% \text{ Inhibition}$$

The allowable limits of inhibition are 80% or greater.

Preparation of High Specific Activity $^{125}$I-T4 The following solutions were prepared:
A. T4 free acid (4 mg.) was dissolved in 0.05M sodium phosphate buffer (1.0 ml.) by adding 1N sodium hydroxide (40 μl.), then diluted with t-butyl alcohol (9.0 ml.).
B. Chloramine T (2.6 mg.) was dissolved in 0.05M sodium phosphate buffer (1.0 ml.).
C. Sodium metabisulfite (5.0 mg.) was dissolved in sodium phosphate buffer (1.0 ml.).
D. Formic acid (23 ml.) was added to S.P.F. water (77 ml.).
E. Ammonium hydroxide (0.5 ml.) was added to methanol (50 ml.).

Procedure:
1. Solution D was placed in a suitable chromatography chamber and allowed to equilibrate for at least one hour before using.
2. The following were added to a 4cc. vial.
  a. 25 μl. T-4 (solution A 10 μgm)
  b. 5mCi sodium iodide I-125
  c. 25 μl. sodium phosphate buffer
  d. 15 μl. chloramine T (solution B 39 μgm)
  e. react for 60 seconds
  f. 20 μl. sodium metabisulfite (Solution C 100 μgm)
3. A 1 inch Whatman paper chromatography strip was spotted with enough material for a radio-chromatogram.
4. The remainder of the T-4 reaction mix was spotted on another 1 inch Whatman paper chromatograph strip.
5. Both strips were developed in Solution D to a height of 25–30 cm.
6. The T-4 band on the strip from step 4 was located and the T4 extraction with 8–12 ml. of Solution E. Saturated sodium sulfite (150 μl.) was added.
7. The strip from step 3 was scanned to obtain specific activity.
8. The T-4 solution from step 6 was evaporated to dryness using an air stream.
9. The dried T-4 was dissolved with 60 ml. T-3/T-4 diluent (SRS 78).

Preparation of T4-Depleted Serum

The serum T4 is extracted from normal human serum according to the following procedure:
1. Anion exchange resin (1 μg. for each 5 ml. of human serum to be processed; "Amberlite CG-400" marketed by Rohm and Haas Company, 100–200 mesh, quaternary ammonium type, 3.3 meq./g.) is washed in 0.15M saline and the fines removed. It is then filtered through coarse sintered glass.
2. The serum is filtered through 8 μ Millipore Filter (MF) to remove particulate matter and a trace quantity of $^{125}$I-T4 was added sufficient to yield approximately 50–100,000 CPM/ml. as precount.
3. Moist resin was added to the serum contained in a glass vessel such that the depth of the mixture is minimized; a stirring bar is placed in the vessel and the contents are mixed slowly at 4° C. for 16–20 hours; the speed of the stirrer should be such as to just prevent the contents from settling out and the stir bar is selected for utilization of as much of the vessel diameter as possible.
4. The mixture was centrifuged at 10,000 RPM (rotor #5534, Sorvall, radius 5.25 inches) for 1 hour at 4° C. ± 2° C. The supernatant was carefully decanted into a MF (8 μ pore diameter and the filtrate collected at 4° C.; the filtration was repeated with a 3μMF and then with a 0.22μMF as above. 1 ml. of the final filtrate is counted.

Approx. yield = 70% or greater.
The allowable limit for extraction efficiency = 92% or greater:

$$\frac{\text{CPM/ml. filtrate}}{\text{CPM/ml. starting material}} \times 100 = A$$

100-A = % T4 extracted

The T4 depleted serum prepared as above is then studied for binding capacity as follows:
1. Veronal buffer (1.09 ml.) is added to each of 2 vials (in duplicate).
2. 100μl. $^{125}$I-T4 (100 pg. ± 20 pg.) is added to each vial.
3. To one vial starting serum (10 μl.) is added and to the other extracted or depleted serum (10 μl.) is added. The vials are mixed by rotation and counted.
4. The vials are incubated at 37° C. for one-half hour (water bath, static).
5. A resin strip is added to each vial and the vials rotated for one-half hour at room temperature (15° C.–32° C.).
6. The strips are carefully removed and the vials are counted.
7. The %T4 bound is calculated for each vial.

$$\frac{\text{CPM post}}{\text{CPM pre}} \times 100 = \% \; ^{125}\text{I-T4 bound}$$

The depleted serum counts should exceed the starting material count by Δ6% or greater. T-4 depleted serum meeting these specifications is then made up to 0.6% sodium azide concentration and stored at 4° C. until the standards are to be prepared.

Preparation of T4 Standards

The starting material is free acid thyroxine. A solution of T4 in methanolic ammonium hydroxide is chromatographed to estimate contamination with T3 and the lots showing appreciable T3 content are rejected.

1. 10 mg. of T4 which has been stored at −20° C. in vacuum is accurately weighed out and made up to 100μg./ml. in a mixture of methanol and NH₄OH (99:1) (Solution 1).

2. To Solution 1 (1.0 ml.) is added veronal buffer (99 ml.) previously warmed to 37° C. (Solution 2 = 1μg./ml.).

3. The volumes of Solution 2 given below are added to give the concentrations indicated; the additions should be made to 50 ml. volumetric flasks which have been thoroughly rinsed with T4 depleted serum.

| Conc. μg/ml. | Conc. μg % | Conc. Adjusted* μg % | Solution 2 (ml.) |
|---|---|---|---|
| .04 | 4 | 40 | 2 |
| .02 | 2 | 20 | 1 |
| .01 | 1 | 10 | 0.5 |
| .005 | 0.5 | 5 | 0.25 |
| .002 | 0.2 | 2 | 0.1 |
| .001 | 0.1 | 1 | 0.5 |

*Since 1/10 quantity (10 μl) of test serum is used, the standards are made up to contain 1/10 the T4.

4. The T4 depleted serum is added to 50 ml. and stored at 4° C.

Preparation of T4 Immunogen and T4 Antiserum

Crystalline bovine serum albumin (BSA; 150 mg.) was weighed out and dissolved in distilled water (75 ml.) at 2°–8° C. N-acetyl derivative of T4 (100 mg., Fox Chemical Co.) was weighed out and dissolved with warming to 37° C. in dimethyl formamide (34 ml.). When dissolved, 2.7–4.5 μCi $^{125}$I-T4 is added and mixed. 1-ethyl-3-(3-dimethylaminopropyl)-carbodiimide (ECDI; 100 mg.) are weighed out and dissolved in distilled water (2 ml.) at room temperature. With the BSA solution in a vessel containing a magnetic stir bar, the ECDI solution is added and gently stirred. The pH is adjusted to 5.8 with 0.05N HCl and 0.05N NaOH. After 1 hour, additional ECDI (50 mg.) in solid form is added. The pH, which tends to rise, is maintained at 5.8 after addition of the T4 dropwise. After 2 hours, the reaction vessel is wrapped in aluminum foil and stirred for 18–24 hours at 2°–8° C.

The reaction mixture (1 ml.) is counted and the volume determined to the nearest 0.1 ml. The reaction mixture is placed in a cellophane dialysis membrane and dialyzed against distilled water for 3 days with frequent changes of water; the ratio of dialysis water to reaction mixture should be at least 15:1, the cloudy solution is removed from the dialysis sac, 1 ml. is counted and the volume is determined to the nearest 0.1 ml. The mg T4 bound is calculated as follows:

$$\frac{\text{CPM (pre-dialysis)} \times \# \text{ ml.}}{\text{CPM (post-dialysis)} \times \# \text{ ml.}} \times 100 = \text{mg.} \frac{T4}{150} \text{ mg. BSA}$$

$$\frac{\text{Moles T4 bound}}{\text{Moles BSA}} = \frac{x}{1} = \text{molar ratio} \frac{T4}{BSA},$$

The molar ratio must be at least 10:1.

The immunogen preparation thus produced is lyophilized at 5μ or less for 48 hours; for doing so, the material is dispensed in 9 mg. BSA quantities. For the immunization the freeze dried preparation is resuspended in distilled water (3 ml.) and the insoluble suspension is triturated by high speed homogenization (Virtis homogenizer, full speed). Complete Freund's adjuvant (3 ml.) is added and the mixture emulsified by high speed homogenization. After a pre-immunization bleed, the animals are injected at 2 sites subcutaneously in the thoracic region (in the case of goats and sheep) with a total dose of about 3 mg. and with 0.5 ml. at 4 sites, subcutaneously or intramuscularly in femoris muscle, subscapular region and thoracic region (in the case of rabbits) with a total dose equal to about 3 mg. The immunization is repeated at 2–3 week intervals and sample sera are tested periodically by titration. When the antibody titer is 10,000 or greater, the animal is bled for large volume and the antiserum obtained.

The antisera are stored lyophilized in 0.2 cc. and 1.0 cc. quantities. Using the 0.2 cc. quantity, for example, the T4 antiserum is reconstituted by adding cold, distilled water (0.2 cc.). Dilutions are prepared in veronal-0.1% HSA buffer solution to bracket the anticipated titer; that is, the dilution of antiserum binding 50% of the T4* in the presence of matrix containing magnesium 8-anilino-1-naphthalene sulfonate and the labeled T4 and in the presence of T4-depleted serum. A sample protocol in which individual components are added rather than the matrix is given below:

| Components | #1 | 2 | 3 | 4 | 5 | 6 |
|---|---|---|---|---|---|---|
| Ml. veronal-0.1% HSA buffer | 0.89 | — | — | — | — | — |
| Ml. Mg ANS (6 mg./ml.) | 0.1 | — | — | — | — | — |
| Ml. T4 depleted serum | 0.01 | — | — | — | — | — |
| Ml. antiserum dilution | 0.1 | — | — | — | — | — |
| dilution antiserum | 10 | 100 | 500 | 1000 | 5000 | 10,000 |
| Ml. $^{125}$I-T4 (1000 pg./ml.) | 0.1 | — | — | — | — | — |

The vials are rotated for 1 minute and the precount is then performed. The vials are incubated for one-half hour at 37° C. in a water bath. A resin strip is added to each vial and the vials rotated for one-half hour at room temperature. The strips are removed and the vials are postcounted. The % $^{125}$I-T4 bound is determined:

$$\frac{\text{Post CPM}}{\text{Pre CPM}} \times 100 = \% \, ^{125}\text{I-T4 bound}$$

The values of %T4* bound are plotted on the ordinate vs. dilution and from the graph the dilution at which 50% of the label is bound is found (50% end point).

Preparation of Kit Components and Kit

A. Reaction Vials: To 8 vols. veronal buffer add 1 vol. $^{125}$I-T4 solution (100 pg. ± 20 pg./0.1 ml.) and 1 vol. Mg ANS solution (6 mg./ml.) both in veronal buffer solution. Mix thoroughly and dispense in 1 ml. aliquots. The vials are stored at 4° C.

B. T4 Antiserum: 5 ml. serum vials with lyophil stoppers are employed. From the titration graph, the dilution giving 65–80% binding of T4* is read. If this titer is, for example, 1:1200, a 1:600 dilution is prepared in double strength veronal buffer (0.150 M). 275 ml. is added to the serum vials and lyophilized with lyophil stoppers set correctly. For use, the lyophilized antibody is reconstituted in distilled water with 5.5 ml. The lyophilized antibody is stored at 4° C.

C. T4 depleted serum-T4 standards prepared as described above.

D. Ion-exchange resin strips are stored immersed in 0.9% saline (50 strips/bottle).

A typical packaged test kit contains the following components:

1. 125 reaction vials (1 ml.) containing less than 0.1 microcurie thyroxine I-125 on date of calibration, 600 micrograms magnesium 8-anilino-1-naphthalene sulfonate and 0.075 molar veronal buffer solution.

2. Vials containing T4 standards containing 1.0, 2.0, 5.0, 10.0, 20.0 and 40.0 micrograms percent T4 in T4-free human serum, 0.5 milliliter per vial.

3. T4 lyophilized antiserum (rabbit, sheep or goat thyroxine antibody in a dilution of greater than 1:100). Each vial contains 0.075M veronal buffer and 0.1% human serum albumin. The reconstituted volume is 5.5 ml.

4. Ion-exchange resin strips.

T4 Radioimmunoassay Test Method

The following procedure is employed in carrying out the T4 radioimmunoassay method of the invention.

1. The lyophilized antiserum is reconstituted with 5.5 ml. of distilled water. The required test components are removed from the refrigerator and allowed to equilibrate to room temperature (15° C. to 32° C.). The reaction vials are mixed by gently swirling. Preferably, the test is carried out in duplicate.

2. During the temperature equilibration period in step 1, the several reaction vials are precounted for a period sufficient to accumulate a minimum of 10,000 counts. The Net CPM Precount is determined and recorded.

3. 10 Microliters each of the 1.0, 2.0, 5.0, 10.0, 20.0 and 40.0 micrograms percent standards is added to a series of reaction vials and 10 microliters of the patient's serum is added to each of the other reaction vials using 10-microliter micropipets.

4. 100 Microliters of antiserum is added to each reaction vial and the caps are replaced. This may be accomplished by a semi-automatic microliter pipet or a repeating microliter syringe.

5. The vials are incubated for a minimum of 30 minutes not to exceed 40 minutes in a 37° C. water bath (filled to a depth equal to or slightly greater than the reaction vial solution level). The reaction time must be equal for all reaction vials.

6. The reaction vials are removed from the water bath. One resin strip is inserted in each reaction vial and the caps are replaced.

7. The reaction vials are rotated for a minimum of 30 minutes not to exceed 40 minutes at room temperature (15° C. to 32° C.) on a rotator which produces end-over-end mixing at 12 to 14 rpm. The separation time must be equal for all reaction vials.

8. The resin strips are removed immediately and discarded. The resin strips should be allowed to drain over the vials by touching the strip lightly on top of the vials. The caps are replaced.

9. Each reaction vial is postcounted for a period sufficient to accumulate a minimum of 10,000 counts. The Net CPM Postcount is determined and recorded.

10. The Net CPM Postcount in each reaction vial (step 9) is divided by the average Net CPM Precount (step 2). The quotient is the Percent Thyroxine I-125 Bound to the antibody.

$$\text{Percent Thyroxine I-125 Bound} = \frac{\text{Net CPM Postcount (Step 9)}}{\text{Net CPM Precount (Step 2)}} \times 100$$

11. The average percent bound of the duplicate values of each standard on the linear axis of semilogarithmic graph paper is plotted as a function of the concentration of the standards in micrograms percent.

12. The percent bound value of each patient's serum is determined. The thyroxine concentration for that percent bound value is determined from the standard curve (e.g., see FIG. 2).

The standard curve shown in FIG. 2 was prepared by plotting the following numbers:

| Thyroxine Standard ($\mu$g %) | Average Net CPM Precount | Average Net CPM Postcount | Percent Thyroxine I-125 Bound |
|---|---|---|---|
| 1.0 | 36,997 | 27,415 | 74.1 |
| 2.0 | | 26,379 | 71.3 |
| 5.0 | | 23,160 | 62.6 |
| 10.0 | | 18,683 | 50.5 |
| 20.0 | | 13,837 | 37.4 |
| 40.0 | | 9,730 | 26.3 |

By this radioimmunoassay method, the euthyroid range was found to be 4.5–12.0 $\mu$g% T4 with a mean of 7.4 ± 1.8. Hyperthyroid patients were found to have a mean of 17.1 ± 4.8 $\mu$g%. Hypothyroid patients were found to have a mean of 2.7 ± 1.5 $\mu$g%. Utilizing this normal range, serum T4 levels were found to be elevated in 92 percent of the patients who were clinically hyperthyroid. For those patients who were clinically hypothyroid, 88 percent were found to have serum T4 levels below the normal range.

In patients who were pregnant or receiving estrogen therapy, the mean serum T4 was found to be 11.0 ± 1.4 $\mu$g% and 10.9 ± 2.8 $\mu$g% respectively, i.e., in the upper normal range. In patients receiving androgen medication, the mean serum T4 was found to be 4.3 ± 1.0 $\mu$g%.

In the newborn the mean serum T4 was found to be 19.5 ± 5.1 $\mu$g%.

The following data were obtained using a representative kit and represent the mean and standard deviation for each set of six replicate determinations made on each of seven different days for control sera with known concentrations of T4.

| Control Serum I | Day 1 | Day 2 | Day 3 | Day 4 | Day 5 | Day 6 | Day 7 |
|---|---|---|---|---|---|---|---|
| Control (actual T4 $\mu$g %) Mean | | | | 4.0 | | | |
| Determined T4 $\mu$g % (M = 6) | 3.3 | 3.8 | 3.8 | 3.7 | 4.4 | 3.7 | 3.6 |
| Standard Deviation ($\mu$g %) | 0.3 | 0.3 | 0.3 | 0.3 | 0.2 | 0.2 | 0.2 |
| Control Serum II | Day 1 | Day 2 | Day 3 | Day 4 | Day 5 | Day 6 | Day 7 |
| Control (actual T4 $\mu$g %) Mean | | | | 8.0 | | | |
| Determined T4 $\mu$g % | 7.6 | 8.0 | 7.9 | 7.9 | 7.9 | 7.5 | 7.6 |

-continued

| | Day 1 | Day 2 | Day 3 | Day 4 | Day 5 | Day 6 | Day 7 |
|---|---|---|---|---|---|---|---|
| (N = 6) Standard Deviation (μg %) | 0.3 | 0.4 | 0.2 | 0.3 | 0.2 | 0.4 | 0.5 |
| Control Serum III | Day 1 | Day 2 | Day 3 | Day 4 | Day 5 | Day 6 | Day 7 |
| Control (actual T4 μg %) | | | | 12.0 | | | |
| Mean Determined T4 μg % (N = 6) | 11.1 | 12.9 | 11.1 | 11.1 | 12.3 | 10.7 | 12.9 |
| Standard Deviation (μg %) | 0.7 | 0.5 | 0.2 | 0.6 | 0.7 | 0.4 | 0.5 |

Intra-Run Variation

The following data were obtained using a representative kit and represent the mean and standard deviation for each set of six replicate determinations made on each of four different days for a hypothyroid, euthyroid, and hyperthyroid control serum.

| Hypothyroid Control Serum | Day 1 | Day 2 | Day 3 | Day 4 |
|---|---|---|---|---|
| Mean T4 value (μg %) (N = 6) | 2.8 | 3.4 | 2.7 | 3.2 |
| Standard Deviation (μg %) | 0.3 | 0.6 | 0.5 | 0.2 |

| Euthyroid Control Serum | Day 1 | Day 2 | Day 3 | Day 4 |
|---|---|---|---|---|
| Mean T4 value (μg %) (N = 6) | 7.2 | 7.1 | 6.6 | 6.8 |
| Standard Deviation (μg %) | 0.2 | 0.4 | 0.5 | 0.5 |

| Hyperthyroid Control Serum | Day 1 | Day 2 | Day 3 | Day 4 |
|---|---|---|---|---|
| Mean T4 value (μg %) (N = 6) | 14.4 | 13.7 | 13.7 | 13.5 |
| Standard Deviation (μg %) | 0.3 | 0.2 | 0.6 | 0.6 |

Inter-Run Variation

The following data were obtained using a representative kit and represent the mean for each set of four replicate determinations, and the mean and standard deviation for the sets of determinations made on four consecutive days for a hypothyroid, euthyroid, and hyperthyroid control serum.

| | Hypothyroid Control Serum Mean μg % T4 (N = 4) | Euthyroid Control Serum Mean μg % T4 (N = 4) | Hyperthyroid Control Serum Mean μg % T4 (N = 4) |
|---|---|---|---|
| Day 1 | 2.8 | 7.2 | 14.4 |
| Day 2 | 3.4 | 7.1 | 13.7 |
| Day 3 | 2.7 | 6.6 | 13.7 |
| Day 4 | 3.2 | 6.8 | 13.5 |
| Mean (N = 16) | 3.0 | 6.9 | 13.8 |
| Standard Deviation | 0.3 | 0.2 | 0.4 |

The sensitivity and reproducibility of the T4 method of the present invention is such that 0.5 micrograms percent T4 is distinguishable between the 1 and 2 micrograms percent standards.

In view of the above, it will be seen that the several objects of the invention are achieved and other advantageous results attained.

As various changes could be made in the above methods and products without departing from the scope of the invention, it is intended that all matter contained in the above description or shown in the accompanying drawing shall be interpreted as illustrative and not in a limiting sense.

What is claimed is:

1. A radioimmunoassay method for the in vitro determination of L-triiodothyronine in unextracted blood serum which comprises the steps of mixing a sample of blood serum whose L-triiodothyronine content is to be determined with a reagent consisting essentially of a buffered solution containing radioactive L-triiodothyronine and an inhibitor for inhibiting binding of L-triiodothyronine to thyroxine-binding globulin, said inhibitor being selected from the group consisting of the magnesium, calcium and alkali metal salts of 8-anilino-1-naphthalene sulfonic acid;

adding to the mixture an antiserum containing antibody capable of immunoreactivity with L-triiodothyronine;

incubating the resultant mixture at a temperature and for a sufficient period of time to produce substantial equilibration of the antibody bound L-triiodothyronine and unbound L-triiodothyronine;

separating the unbound L-triiodothyronine from the antibody bound L-triiodothyronine; and determining the relative amounts of antibody bound radioactive L-triiodothyronine and unbound radioactive L-triiodothyronine.

2. A radioimmunoassay method as set forth in claim 1 wherein said incubation step is carried out at a temperature of 37° C. for a period of approximately 1 hour.

3. A radioimmunoassay method as set forth in claim 1 wherein said radioactive L-triiodothyronine is selected from the group consisting of L-triiodothyronine containing iodine-125 and L-triiodothyronine containing iodine-131.

4. A radioimmunoassay method as set forth in claim 1 wherein the unbound L-triiodothyronine is separated from the antibody bound L-triiodothyronine by contacting the mixture with a relatively thin strip of a membrane consisting essentially of an ion-exchange resin for a predetermined length of time.

5. A radioimmunoassay method as set forth in claim 4 wherein said mixture is maintained in contact with said membrane for a period of approximately one hour at room temperature.

6. A radioimmunoassay method for the in vitro determination of L-triiodothyronine in unextracted blood serum which comprises the steps of mixing a sample of blood serum whose L-triiodothyronine content is to be determined with a reagent consisting essentially of a buffered solution containing radioactive L-triiodothyronine containing iodine-125 and magnesium 8-anilino-1-naphthalene sulfonate;

adding to the mixture an antiserum containing antibody capable of immunoreactivity with L-triiodothyronine;

incubating the resultant mixture at a temperature of 37° C. for a period of approximately one hour to produce substantial equilibration of the antibody bound L-triiodothyronine and unbound L-triiodothyronine;

adding a relatively thin strip of a membrane consisting essentially of an ion-exchange resin to the mixture and maintaining said membrane in contact therewith for a period of approximately one hour at room temperature to separate the unbound L-triiodothyronine from the antibody bound L-triiodothyronine; and determining the relative amounts of antibody bound radioactive L-triiodothyronine and unbound radioactive L-triiodothyronine.

7. A radioimmunoassay method for the in vitro determination of L-triiodothyronine in unextracted blood serum which comprises the steps of mixing a sample of blood serum whose L-triiodothyronine content is to be determined with a reagent consisting essentially of a buffered solution containing radioactive L-triiodothyronine, an inhibitor for inhibiting binding of L-triiodothyronine to a thyroxine-binding globulin, said inhibitor being selected from the group consisting of the magnesium, calcium and alkali metal salts of 8-anilino-1-naphthalene sulfonic acid, and an antiserum containing antibody capable of immunoreactivity with L-triiodothyronine;

incubating the resultant mixture at a temperature and for a sufficient period of time to produce sustantial equilibration of the antibody bound L-triiodothyronine and unbound L-triiodothyronine;

separating the unbound L-triiodothyronine from the antibody bound L-triiodothyronine; and determining the relative amounts of antibody bound radioactive L-triiodothyronine and unbound radioactive L-triiodothyronine.

8. A radioimmunoassay method as set forth in claim 7 wherein said incubation step is carried out at a temperature of 37° C. for a period of approximately 1 hour.

9. A radioimmunoassay method as set forth in claim 7 wherein said radioactive L-triiodothyronine is selected from the group consisting of L-triiodothyronine containing iodine-125 and L-triiodothyronine containing iodine-131.

10. A radioimmunoassay method as set forth in claim 7 wherein the unbound L-triiodothyronine is separated from the antibody bound L-triiodothyronine by contacting the mixture with a relatively thin strip of a membrane consisting essentially of an ion-exchange resin for a predetermined length of time.

11. A radioimmunoassay method as set forth in claim 10 wherein said mixture is maintained in contact with said membrane for a period of approximately one hour at room temperature.

12. A radioimmunoassay method for the in vitro determination of L-triiodothyronine in unextracted blood serum which comprises the steps of mixing a sample of blood serum whose L-triiodothyronine content is to be determined with a reagent consisting essentially of a buffered solution containing radioactive L-triiodothyronine containing iodine-125, magnesium 8-anilino-1-naphthalene sulfonate and an antiserum containing antibody capable of immunoreactivity with L-triiodothyronine;

incubating the resultant mixture at a temperature of 37° C. for a period of approximately one hour to produce substantial equilibration of the antibody bound L-triiodothryonine and unbound L-triiodothyronine;

adding a relatively thin strip of a membrane consisting essentially of an ion-exchange resin to the mixture and maintaining said membrane in contact therewith for a period of approximately one hour at room temperature to separate the unbound L-triiodothyronine from the antibody bound L-triiodothyronine; and determining the relative amounts of antibody bound radioactive L-triiodothyronine and unbound radioactive L-triiodothyronine.

13. A reagent for use in a radioimmunoassay method for the in vitro determination of L-triiodothyronine in unextracted blood serum consisting essentially of a buffered solution containing radioactive L-triiodothyronine and an inhibitor for inhibiting binding of L-triiodothyronine to thyroxine-binding globulin, said inhibitor being selected from the group consisting of the magnesium, calcium and alkali metal salts of 8-anilino-1-naphthalene sulfonic acid.

14. A reagent as set forth in claim 13 wherein said radioactive L-triiodothyronine is selected from the group consisting of L-triiodothyronine containing iodine-125 and L-triiodothyronine containing iodine-131.

15. A reagent for use in a radioimmunoassay method for the in vitro determination of L-triiodothyronine in unextracted blood serum consisting essentially of a buffered solution containing radioactive L-triiodothyronine, an inhibitor for inhibiting binding of L-triiodothyronine to thyroxine-binding globulin, said inhibitor being selected from the group consisting of the magnesium, calcium and alkali metal salts of 8-anilino-1-naphthalene sulfonic acid, and an antiserum containing antibody capable of immunoreactivity with L-triiodothyronine.

16. A reagent as set forth in claim 15 wherein said radioactive L-triiodothyronine is selected from the group consisting of L-triiodothyronine containing iodine-125 and L-triiodothyronine containing iodine-131.

* * * * *